(12) United States Patent
Chia et al.

(10) Patent No.: US 7,104,796 B1
(45) Date of Patent: Sep. 12, 2006

(54) DISPOSABLE PROPHY ANGLE FOR AN ELECTRIC TOOTH POLISHER

(75) Inventors: Hui-Tsu Chia, No. 7, Alley 2, Lane 164, Sec. 1, Hsiafu Rd., Tucheng City, Taipei Hsien (TW); Shui-Tao Tseng, Zhongshan (CN); Philip Phung-I Ho, 2780 State St., Suite#7, Santa Barbara, CA (US) 93105

(73) Assignees: Hui-Tsu Chia, Taipei Hsien (TW); Meditech International Co., Ltd., Zhongshan (CN); Philip Phung-I Ho, Santa Barbara, CA (US)

( * ) Notice: Subject to any disclaimer, the term of this patent is extended or adjusted under 35 U.S.C. 154(b) by 0 days.

(21) Appl. No.: 11/248,281

(22) Filed: Oct. 13, 2005

(51) Int. Cl.
*A61C 3/06* (2006.01)
(52) U.S. Cl. ..................................... 433/125
(58) Field of Classification Search ............. 433/125, 433/126, 166, 114
See application file for complete search history.

(56) References Cited

U.S. PATENT DOCUMENTS

| | | | | | |
|---|---|---|---|---|---|
| 2,226,145 | A | * | 12/1940 | Smith | ............................ 15/29 |
| 2,707,329 | A | * | 5/1955 | Costoff | ....................... 433/166 |
| 6,053,732 | A | * | 4/2000 | Sale | .......................... 433/125 |
| 6,766,549 | B1 | * | 7/2004 | Klupt | ......................... 15/22.2 |

* cited by examiner

*Primary Examiner*—Melba N. Bumgarner
(74) *Attorney, Agent, or Firm*—Rabin & Berdo, P.C.

(57) ABSTRACT

A disposable prophy angle is mounted to an electric tooth polisher that has a controller, a handle having a motor and a driving shaft. The prophy angle is mounted to the handle and has a casing, a driven shaft, a surface-polishing member and a crevice-cleaning member. The casing is mounted to the handle and has a cavity and a distal open end. The driven shaft is mounted rotatably in the casing, rotates in response to the motor and has a mount. The surface-polishing and crevice-cleaning members are detachably mounted on the mount simultaneously. The tooth polisher with both the surface-polishing and crevice-cleaning members can be used to clean teeth without the need to replace the members and is timesaving.

5 Claims, 6 Drawing Sheets

DISPOSABLE PROPHY ANGLE FOR AN ELECTRIC TOOTH POLISHER

BACKGROUND OF THE INVENTION

1. Field of the Invention

The present invention relates to a tooth cleaner, and more particularly to a disposable prophy angle for an electric tooth polisher. The disposable prophy angle has a mount, a disposable surface-polishing member and a disposable crevice-cleaning member. The members are detachably mounted to the mount simultaneously.

2. Description of the Related Art

Electric tooth polishers are generally tools used by dentists to clean teeth.

With reference to FIG. 6, a conventional electric tooth polisher has a controller (70), a handle (80) and a disposable prophy angle.

The controller (70) is connected to a power source and has a display and a switch.

The handle (80) is connected to the controller (70) through a cable and has a motor.

With further reference to FIGS. 7 to 9, the disposable prophy angle is connected to the handle (80) and has a hollow casing (90), a driven shaft (91), a mount (92), a disposable surface-polishing member (93) and a disposable crevice-cleaning member (94). The driven shaft (91) is mounted rotatably in the casing (90), rotates in response to the motor and has a distal end extending out of the casing (90). The mount (92) is mounted to the distal end of the driven shaft (91). The surface-polishing member (93) is mounted detachably on the mount (92) and rotates to polish the surface of teeth when the tooth polisher is used. The crevice-cleaning member (94) is conical, may replace the surface-polishing member (93) on the mount (92) and rotates to clean the crevices between adjacent teeth.

However, only one of the attachments, the surface-polishing member (93) or the crevice-cleaning member (94), is used on the prophy angle at any one time. To complete the cleaning process, the polishing and then the crevice cleaning, a dentist must replace one of the members (93, 94) with the other during the treatment. The need to change the members (93, 94) is time wasting.

To overcome the shortcomings, the present invention provides a disposable prophy angle for an electric tooth polisher to mitigate or obviate the aforementioned problems.

SUMMARY OF THE INVENTION

The main objective of the invention is to provide a disposable prophy angle for an electric tooth polisher. The disposable prophy angle has a mount, a disposable surface-polishing member and a disposable crevice-cleaning member. The members are detachably mounted to the mount simultaneously.

The disposable prophy angle in accordance with the present invention is mounted to an electric tooth polisher that has a controller and a handle having a motor and a driving shaft.

The prophy angle is mounted to the handle and has a casing, a driven shaft, a surface-polishing member and a crevice-cleaning member.

The casing is mounted to the handle and has a cavity and a distal open end.

The driven shaft is mounted rotatably in the casing, rotates in response to the motor and has a mount.

The surface-polishing and crevice-cleaning members are detachably mounted on the mount simultaneously.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
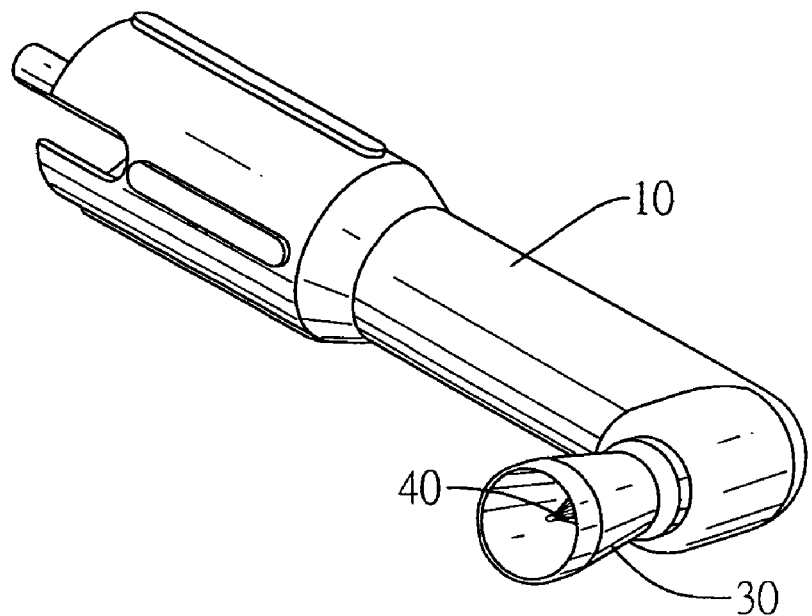
FIG. 1 is a perspective view of a disposable prophy angle for an electric tooth polisher in accordance with the present invention.

A disposable prophy angle in accordance with the present invention is mounted to an electric tooth polisher. The electric tooth polisher has a controller and a handle. The controller is connected to a power source. The handle is connected to the controller through a cable and has a motor and a driving shaft rotatably mounted to the motor.

With reference to FIGS. 1 to 5, the disposable prophy angle in accordance with the present invention has a casing (10), a driven shaft (20, 20a, 20b, 20c), a surface-polishing member (30, 30a, 30b, 30c) and a crevice-cleaning member (40, 40a, 40b, 40c).

The casing (10) is hollow, is mounted to the handle, holds the driving shaft and has a cavity and a distal open end.

The driven shaft (20, 20a, 20b, 20c) is mounted rotatably in the casing (10), engages the driving shaft, rotates in response to the motor and has a mount (21), a proximal engaging element (23, 23a, 23b, 23c) and a distal engaging element (25, 25a, 25b, 25c). The mount (21) is formed axially on the driven shaft (20, 20a, 20b, 20c), extends out of the distal open end of casing (10) and has a distal end. The proximal engaging element (23, 23a, 23b, 23c) is formed on the mount (21). The distal engaging element (25, 25a, 25b, 25c) is formed on the mount (21) close to the distal end of the mount (21).

The surface-polishing member (30, 30a, 30b, 30c) is annular and resilient, is mounted detachably around the mount (21) and polishes the surface of teeth when driven to rotate. The surface-polishing member (30, 30a, 30b, 30c)

has an axial through hole (31), an inner surface and an engaging element (35, 35a, 35c, 35d). The engaging element (35, 35a, 35b, 35c) detachably engages the proximal engaging element (23, 23a, 23b, 23c) on the mount (21) of the driven shaft (20).

The crevice-cleaning member (40, 40a, 40b, 40c) is conical and resilient, is mounted detachably on the mount (21) of the driven shaft (20, 20a, 20b, 20c) in the axial through hole (31) of the surface-polishing member (30, 30a, 30b, 30c) and cleans crevices between adjacent teeth when driven to rotate. The crevice-cleaning member (40, 40a, 40b, 40c) has an engaging element (45, 45a, 45b, 45c). The engaging element (45, 45a, 45b, 45c) detachably engages the distal engaging element (25, 25a, 25b, 25c) on the mount (21) of the driven shaft (20, 20a, 20b, 20c).

Figure 2:
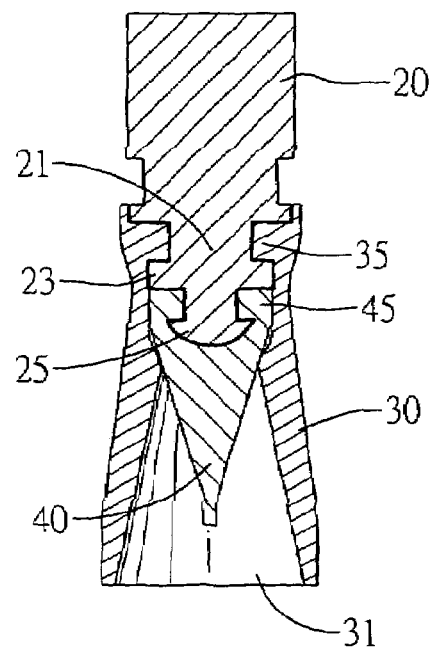
FIG. 2 is an enlarged cross-sectional side view of a first embodiment of the mount with the surface-polishing and crevice-cleaning members of the prophy angle in FIG. 1.

With reference to FIG. 2, a first embodiment of the prophy angle has the proximal engaging element (23) on the mount (21) of the driven shaft (20) being an annular flange. The annular flange extends radially outward from the mount (21) and has a rectangular cross-section and a diameter. The distal engaging element (25) is an enlarged head formed on the distal end of the mount (21) at an interval from the annular flange and having a diameter smaller than that of the annular flange. The engaging element (35) on the surface-polishing member (30) is an annular rib. The annular rib extends radially inward from the inner surface of the surface-polishing member (30), clasps the annular flange on the mount (21) and has a rectangular cross-section. The engaging element (45) on the crevice-cleaning member (40) is an opening on the end of the crevice-cleaning member (40). The opening holds the enlarged head (25) on the mount (21) and has an inner surface and an annular rib. The annular rib of the top opening extends radially inward from the inner surface, clasps the enlarged head (25) and has a rectangular cross-section.

Figure 3:
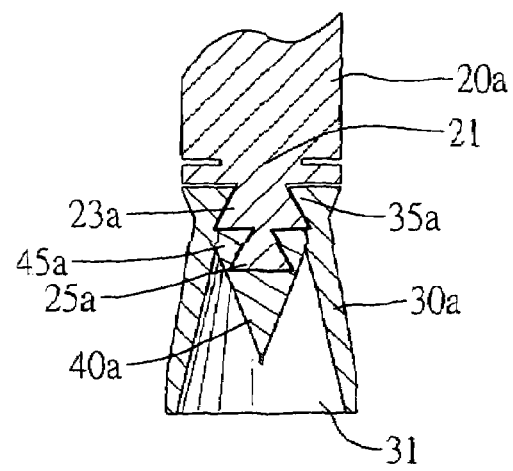
FIG. 3 is an enlarged cross-sectional side view of a second embodiment of the mount with the surface-polishing and crevice-cleaning members of the prophy angle in FIG. 1.

With reference to FIG. 3, a second embodiment of the prophy angle is similar to the first embodiment. However, the proximal engaging element (23a) on the mount (21) is an annular flange having a triangular cross-section. The distal engaging element (25a) is an enlarged head being adjacent to the annular flange and having a triangular cross-section. The engaging element (35a) on the surface-polishing member (30a) is an annular rib having a triangular cross-section. The engaging element (45a) on the crevice-cleaning member (40a) is an opening on the end of the crevice-cleaning member (40a) having an annular rib with a triangular cross-section.

Figure 4:
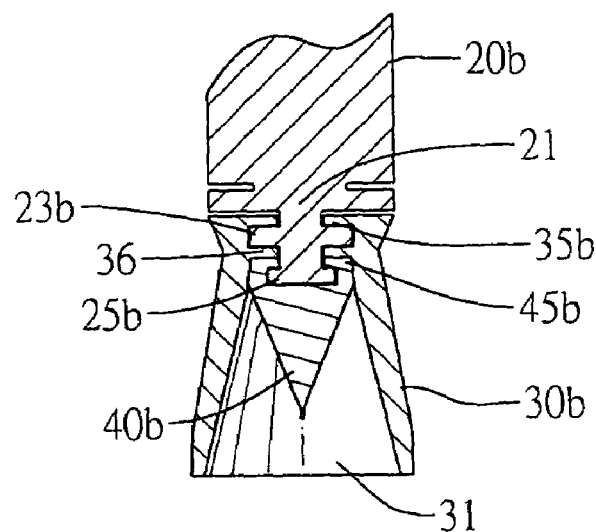
FIG. 4 is an enlarged cross-sectional side view of a third embodiment of the mount with the surface-polishing and crevice-cleaning members of the prophy angle in FIG. 1.

With reference to FIG. 4, a third embodiment of the prophy angle is similar to the first embodiment. However, the surface-polishing element (30b) further has an auxiliary engaging element (36) being an annular rib, extending inward from the inner surface, engaging the interval between the annular flange (23b) and the enlarged head (25b) and being adjacent to the engaging element (45b) of the crevice-cleaning member (40b).

Figure 5:
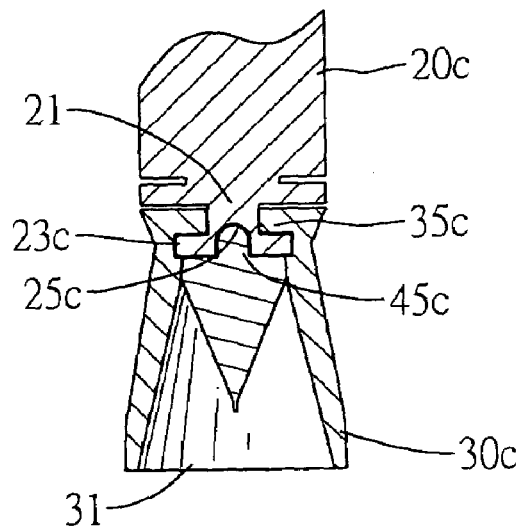
FIG. 5 is an enlarged cross-sectional side view of a fourth embodiment of the mount with the surface-polishing and crevice-cleaning members of the prophy angle in FIG. 1.
Figure 6:
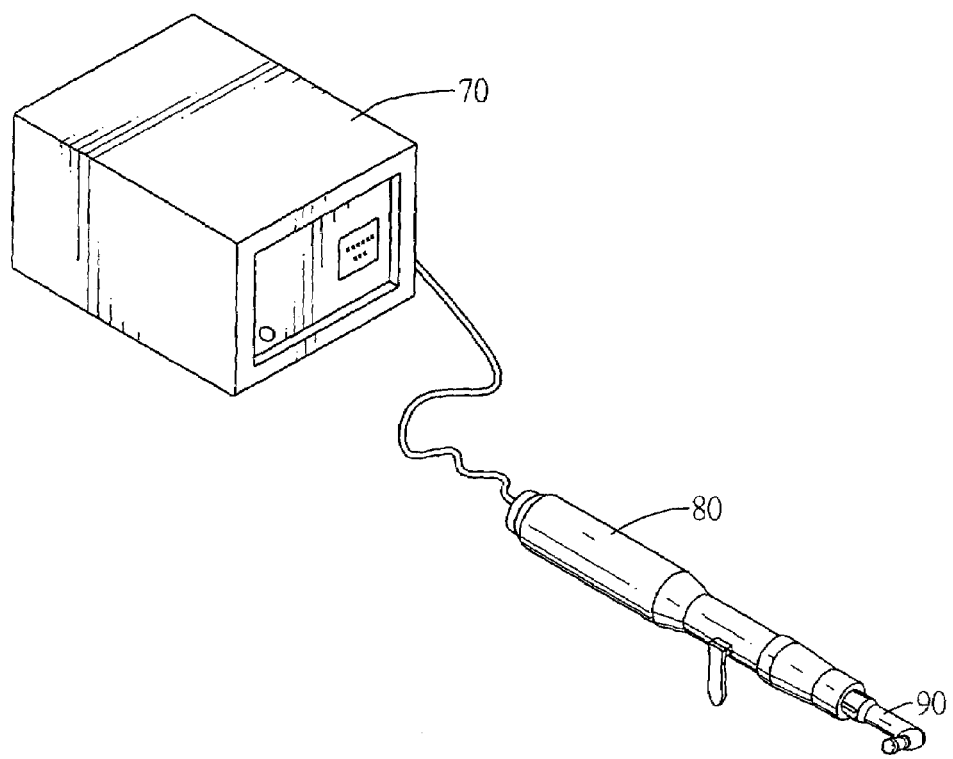
FIG. 6 is a perspective view of a conventional electric tooth polisher in accordance with the prior art.
Figure 7:
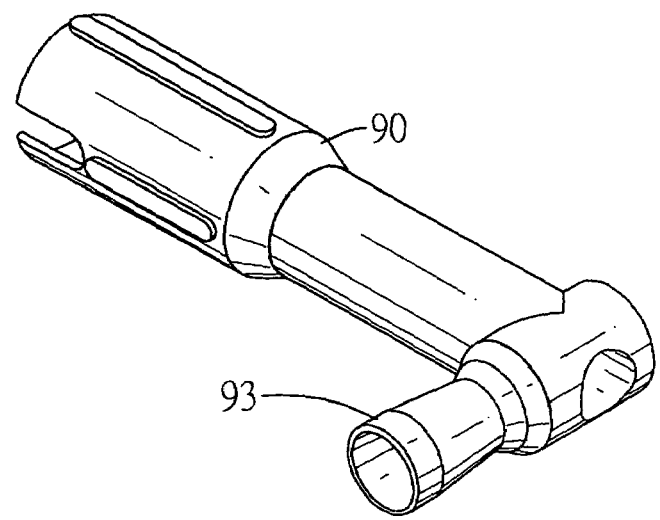
FIG. 7 is a perspective view of the prophy angle of the tooth polisher in FIG. 6.
Figure 8:
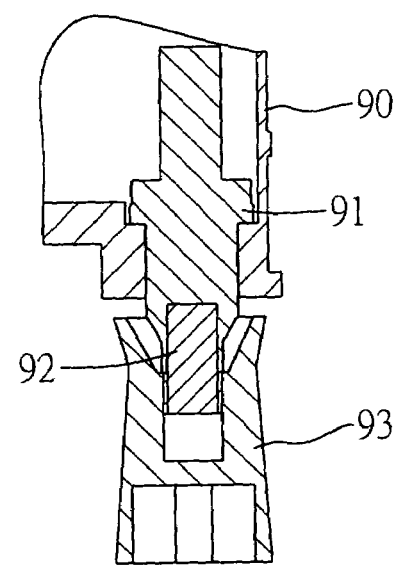
FIG. 8 is an enlarged cross-sectional side view of the prophy angle with the surface-polishing member of the tooth polisher in FIG. 7.
Figure 9:
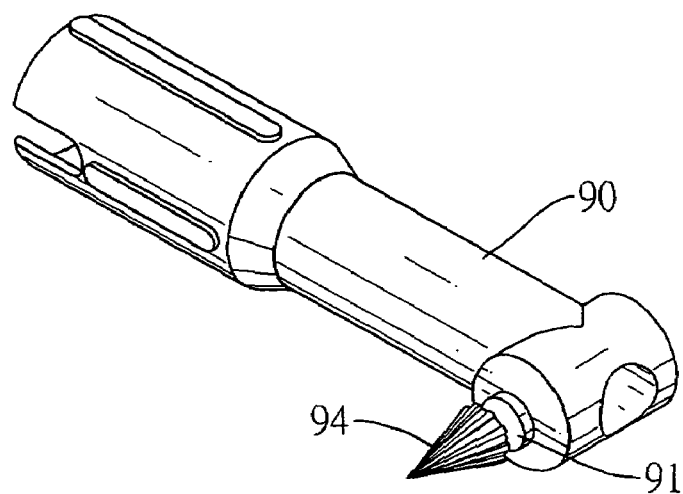
FIG. 9 is a perspective view of the prophy angle with the crevice-cleaning member of the tooth polisher in FIG. 6.
Figure 10:
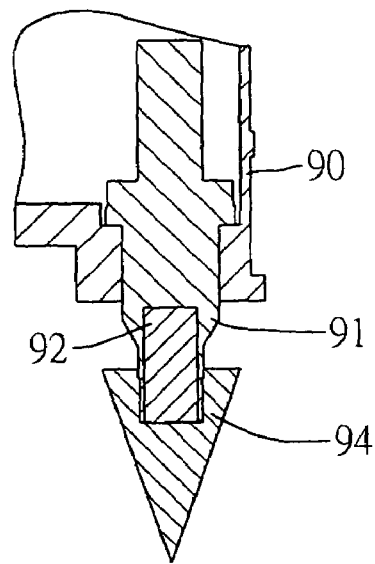
FIG. 10 is an enlarged cross-sectional side view of the prophy angle of the tooth polisher in FIG. 9.

With reference to FIG. 5, a fourth embodiment of the prophy angle is similar to the first embodiment. However, the distal engaging element (25c) is a socket longitudinally defined in the distal end of the mount (21). The engaging element (45c) on the crevice-cleaning member (40c) is a protrusion plugged in the socket.

When the tooth polisher is used to clean teeth, the surface-polishing member (30, 30a, 30b, 30c) of the prophy angle is rotated by the motor to polish the surface of teeth. After the polishing treatment, the surface-polishing member (30, 30a, 30b, 30c) is detached to expose the crevice-cleaning member (40, 40a, 40b, 40c). The crevice-cleaning member (40, 40a, 40b, 40c) is then used to clean the crevices between adjacent teeth.

The prophy angle including both the surface-polishing and crevice-cleaning members (30, 30a, 30b, 30c, 40, 40a, 40b, 40c) can be used without having to either of the members (30, 30a, 30b, 30c, 40, 40a, 40b, 40c) during a treatment. Therefore, using the prophy angle to clean teeth saves time.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A disposable prophy angle mounted to an electric tooth polisher having a controller connected to a power source and a handle connected to the controller through a cable and including a motor and a driving shaft rotatably mounted to the motor, wherein the disposable prophy angle is adapted to be mounted to the handle and comprises:
    a casing being hollow, adapted to be mounted to the handle, adapted to hold the driving shaft and having a cavity and a distal open end;
    a driven shaft mounted rotatably in the casing, adapted to engage the driving shaft, adapted to rotate in response to the motor and having
        a mount formed longitudinally on the driven shaft, extending out of the distal open end of casing and having a distal end;
        a proximal engaging element formed on the mount; and
        a distal engaging element formed on the mount close to the distal end of the mount;
    a surface-polishing member being annular and resilient, mounted detachably around the mount and having an axial through hole, an inner surface and an engaging element detachably engaging the proximal engaging element on the mount of the driven shaft; and
    a crevice-cleaning member being conical and resilient, mounted detachably on the mount of the driven shaft in the axial through hole of the surface-polishing member and having an engaging element detachably engaging the distal engaging element on the mount of the driven shaft.

2. The disposable prophy angle as claimed in claim 1, wherein:
    the proximal engaging element on the mount of the driven shaft is an annular flange extending radially outward from the mount and having a rectangular cross-section and a diameter;
    the distal engaging element on the mount is an enlarged head formed on the distal end of the mount at an interval from the annular flange and having a diameter smaller than that of the annular flange;
    the engaging element on the surface-polishing member is an annular rib extending radially inward from the inner surface of the surface-polishing member, clasping the annular flange on the mount and having a rectangular cross-section; and
    the engaging element on the crevice-cleaning member is an opening in an end of the crevice-cleaning member holding the enlarged head on the mount and having an inner surface; and an annular rib extending radially and inward from the inner surface, clasping the enlarged head and having a rectangular cross-section.

3. The disposable prophy angle as claimed in claim 1, wherein:

the proximal engaging element on the mount of the driven shaft is an annular flange extending radially outward from the mount and having a triangular cross-section and a diameter;

the distal engaging element on the mount is an enlarged head formed on the distal end of the mount adjacent to the annular flange and having a triangular cross-section and a diameter smaller than that of the annular flange;

the engaging element on the surface-polishing member is an annular rib extending radially inward from the inner surface of the surface-polishing member, clasping the annular flange on the mount and having a triangular cross-section; and the engaging element on the crevice-cleaning member is an opening on an end of the crevice-cleaning member holding the enlarged head on the mount and having an inner surface; and an annular rib extending radially and inward from the inner surface, clasping the enlarged head and having a triangular cross-section.

4. The disposable prophy angle as claimed in claim 2, wherein the surface-polishing element further has an auxiliary engaging element being an annular rib, extending inward from the inner surface, engaging the interval between the annular flange and the enlarged head and being adjacent to the engaging element on the crevice-cleaning member.

5. The disposable prophy angle as claimed in claim 1, wherein:

the proximal engaging element on the mount of the driven shaft is an annular flange extending radially outward from the mount;

the distal engaging element on the mount is a socket longitudinally defined in the distal end of the mount;

the engaging element on the surface-polishing member is an annular rib extending radially inward from the inner surface of the surface-polishing member and clasping the annular flange on the mount; and the engaging element on the crevice-cleaning member is a protrusion plugged in the socket.

* * * * *